US00PP29405P3

(12) United States Plant Patent
Tristram

(10) Patent No.: US PP29,405 P3
(45) Date of Patent: Jun. 19, 2018

(54) ***SPIRAEA* PLANT NAMED 'WALPLUM'**

(50) Latin Name: *Spiraea japonica*
Varietal Denomination: Walplum

(71) Applicant: Walberton Plants Ltd., Chichester (GB)

(72) Inventor: David R. Tristram, Arundel (GB)

(73) Assignee: Walberton Plants LTD, Chichester (GB)

( * ) Notice: Subject to any disclaimer, the term of this patent is extended or adjusted under 35 U.S.C. 154(b) by 0 days. days.

(21) Appl. No.: 15/530,742

(22) Filed: Feb. 22, 2017

(65) Prior Publication Data

US 2017/0265344 P1 Sep. 14, 2017

Related U.S. Application Data

(60) Provisional application No. 62/389,769, filed on Mar. 9, 2016.

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Bethany R. Roahrig; Barbara Campbell; Cochran Freund & Young LLC

(57) ABSTRACT

A new cultivar of *Spiraea* named 'Walplum' that is characterized by compact upright habit, deep red-purple new leaf tip growth which becomes olive green as growth continues. The buds of 'Walplum' are red-purple in color and develop into clusters of bright cerise colored flowers in late spring and early summer. 'Walplum' is hardy to USDA Zone 3.

4 Drawing Sheets

Genus and species: *Spiraea japonica.*
Variety denominations: 'Walplum'.

BACKGROUND

The present invention relates to a new and distinct cultivar of *Spiraea*, a deciduous hardy ornamental shrub used for planting in the garden and landscape. The new variety is known botanically as *Spiraea japonica* and will be referred to hereinafter by the cultivar name 'Walplum'.

'Walplum' is the result of a breeding and selection program involving several thousand plants, and carried out by the inventor between 1984 and 1990 at the inventor's nursery in West Sussex, United Kingdom. The objective of the breeding program was to develop compact and stable varieties of *Spiraea japonica* with colorful foliage.

Commencing in 1984, the inventor sowed seeds of self-pollinated plants of *Spiraea japonica* 'Goldflame' (unpatented). The most promising seedling selections were utilized for two subsequent cycles of self-pollination and selection. In 1990, the inventor raised approximately 1,000 seedlings of which the majority were green in color. The inventor observed that approximately ten seedlings exhibited compact forms, smaller leaves, colorful new shoot tips and attractive green foliage and bright flowers when mature. From these seedlings, 'Walplum' was chosen for increase and commercial introduction.

'Walplum' was first asexually propagated by the inventor at the inventor's nursery in West Sussex, United Kingdom in 2012 using softwood cuttings. Since that time, under careful observation, the distinguishing characteristics have been determined stable and uniform in successive generations.

SUMMARY

The following traits have been repeatedly observed and represent the distinguishing characteristics of 'Walplum'. In combination these traits set the new cultivar apart from all other existing varieties of *Spiraea* known to the inventor. 'Walplum' has not been tested under all possible conditions and phenotypic differences may be observed with variations in environmental, climatic, and cultural conditions, without however, any variance in genotype.

1. 'Walplum' exhibits a compact upright habit.
2. A plant of 'Walplum' is 40 cm in height and 40 cm in width after one growing year.
3. A mature plant of 'Walplum' is 60 cm in height and 50 cm in width.
4. The newly-emerging shoot tips of 'Walplum' are deep red-purple in color.
5. The deep red-purple color of the emerging shot tips is most pronounced in early spring and in conditions of full sun.
6. The foliage of 'Walplum' becomes olive green in color as growth continues and as the plant flowers and matures.
7. The buds of 'Walplum' are red-purple in color.
8. The red-purple buds of 'Walplum' develop into clusters of bright cerise colored flowers in late spring and early summer.
9. The fully-open flowers of 'Walplum' bear prominently exserted stamens and anthers.
10. 'Walplum' is hardy to USDA Zone 3.

DESCRIPTION OF THE PHOTOGRAPH

Figure 1:
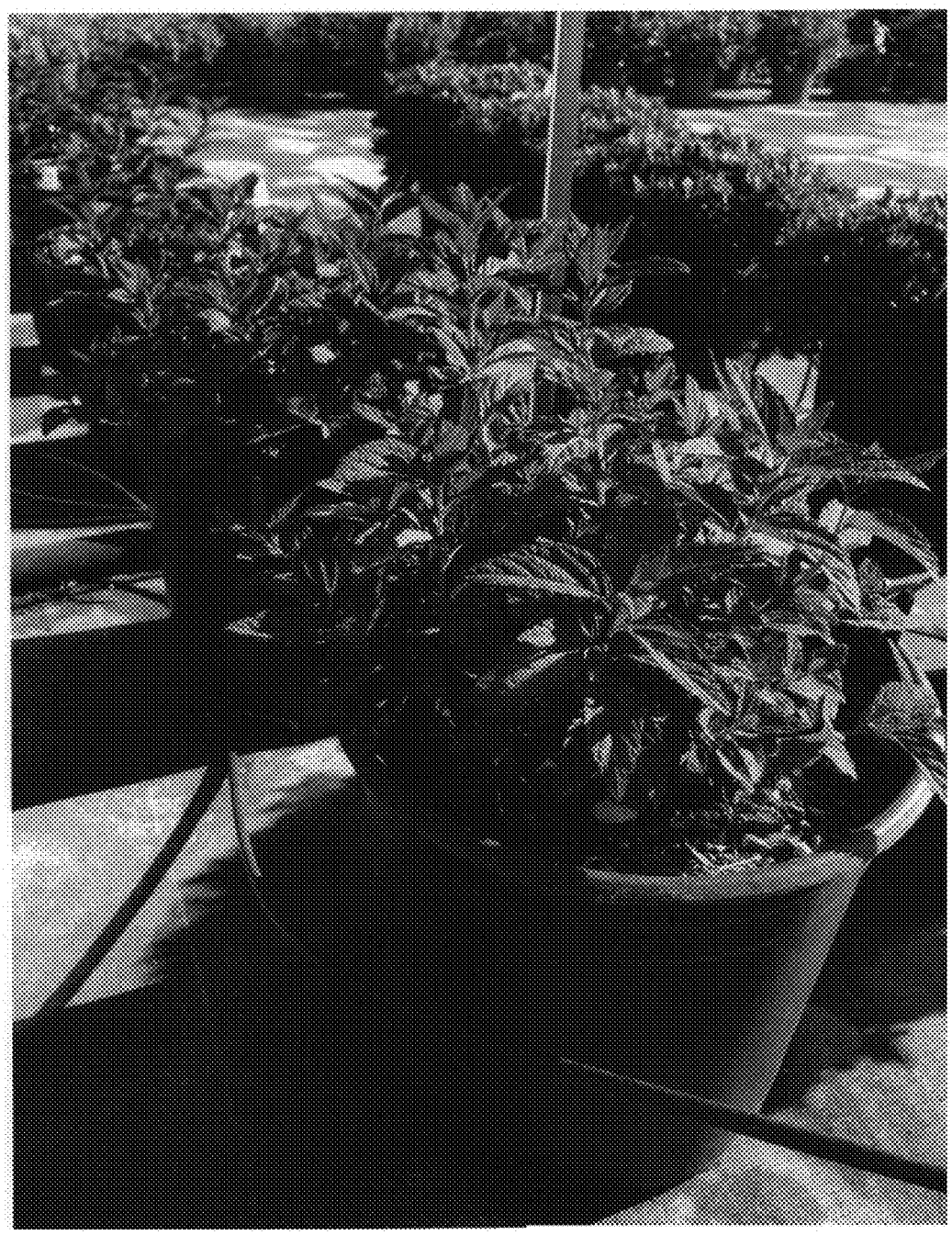

The accompanying color drawing illustrates the overall appearance of the new *Spiraea* cultivar named 'Walplum' showing the colors as true as it is reasonably possible to obtain in colored reproductions of this type The drawing labeled FIG. 1 shows a row of 6 months old plants of 'Walplum' which have been grown outdoors in full sun in Oxnard, Calif. This drawing illustrates the red-purple color of the emerging shoot tips. The illustrated plants are growing in 1 gallon containers and have been grown naturally, without the use of pinching or chemical growth regulator treatments.

Figure 2:
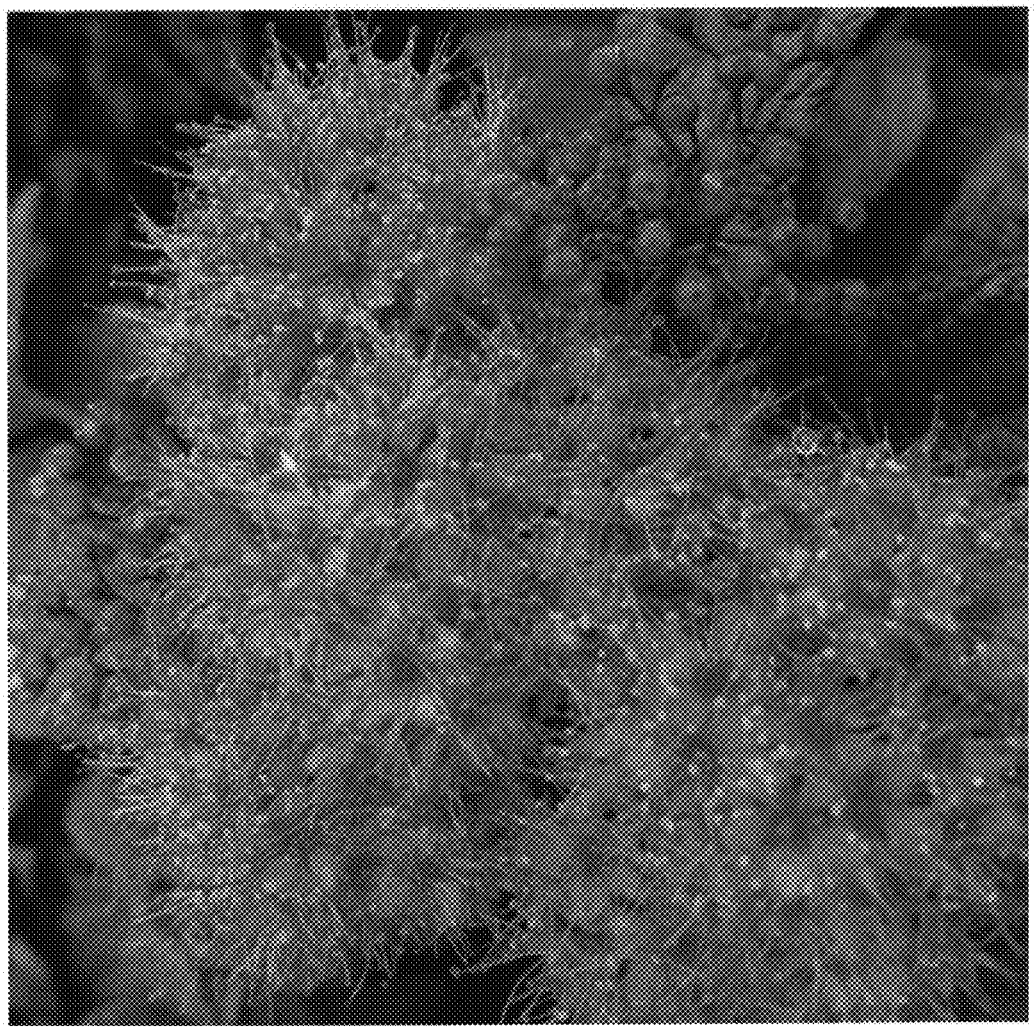

The drawing labeled FIG. 2 shows a close-up view of the inflorescences of 'Walplum'. The drawing has been made from a mature plant growing in a 3 liter containers outdoors at the inventor's nursery in West Sussex, United Kingdom. The drawing illustrates the prominent exserted stamens and anthers of the fully open flowers.

Figure 3:
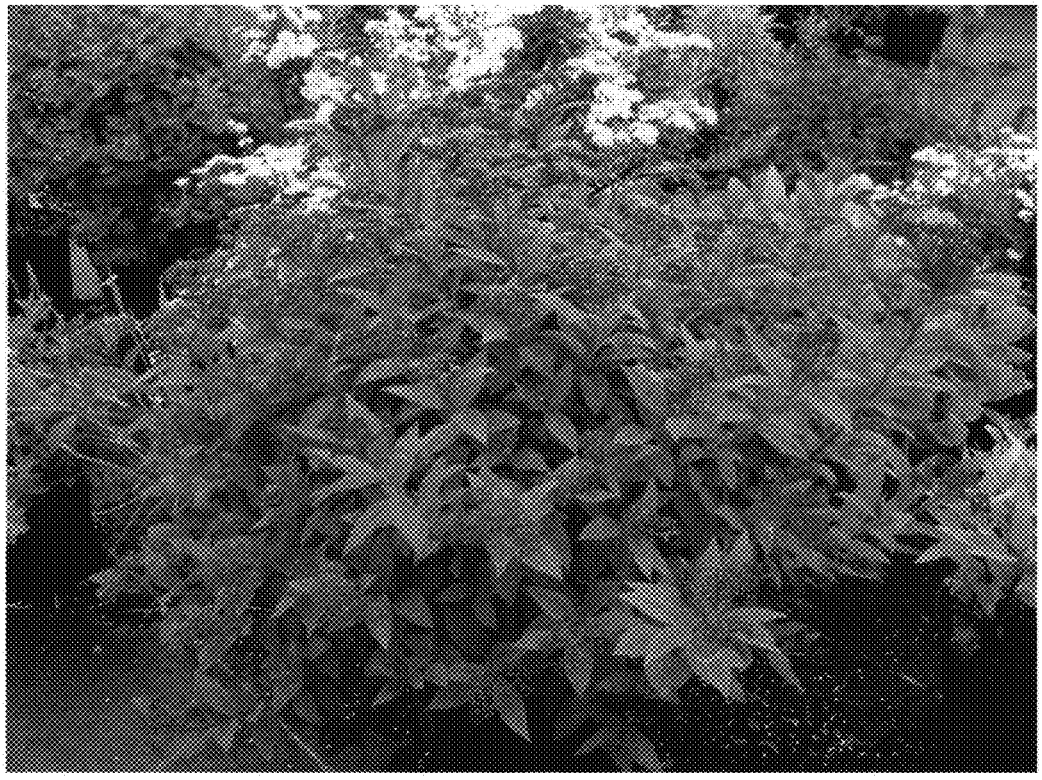

The drawing labeled FIG. 3 shows (in the foreground) a whole plant of 'Walplum'. The drawing has been made from a mature plant growing in a 3 liter container outdoors at the inventor's nursery in West Sussex, United Kingdom. Although the illustrated plant is mature with predominantly green foliage, the newly-emerging shoot tips continue to exhibit their characteristic red-purple color.

Figure 4:
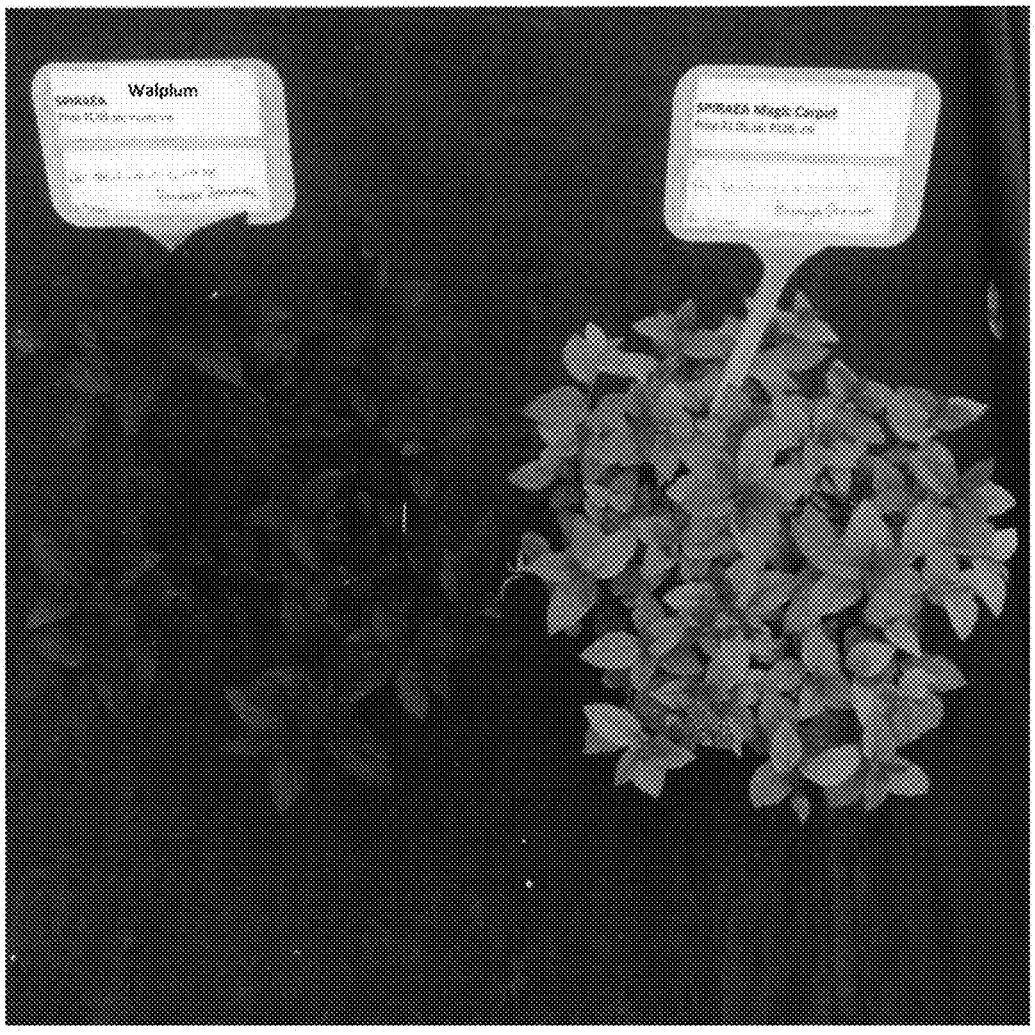

The drawing labeled FIG. 4 compares the appearance of the foliage of 'Walplum' (labeled as *Spiraea* 'Plumtastic') with the foliage of the inventor's variety *Spiraea* 'Magic Carpet' (also known as 'Walbuma'). The drawing has been made from one year old plants growing in a 1 liter container outdoors at the inventor's nursery in West Sussex, United Kingdom.

BOTANICAL DESCRIPTION OF THE PLANT

The following is a detailed description of the *Spiraea* cultivar named 'Walplum'. Data was collected in Oxnard, Calif. from plants grown in one gallon containers outdoors. The plants were approximately 15 months old at the time. Color determinations are in accordance with the Firth Edition (2007) of The Royal Horticultural Society Colour Chart except where general color terms of ordinary dictionary significance are used. The growing requirements are similar to the species. Under normal growing conditions there are no known disease problems known to the inventor.

Botanical classification:

*Genus.*—*Spiraea.*

*Species.*—*japonica.*

*Common name.*—Bridal wreath.

*Variety.*—'Walplum'.

Parentage: Third generation of self-pollinated seedlings originally derived from *Spiraea japonica* 'Goldflame' (unpatented).

Plant description:

*Type.*—Shrub.

*Vigor.*—Vigorous.

*Habit.*—Compact.

*Dimensions* (*after* 1 *year*).—40 cm in height, 40 cm in width.

*Dimensions* (*mature*).—60 cm in height, 50 cm in width.

*Hardiness.*—USDA Zone 3.

*Propagation.*—Softwood cuttings.

*Root system.*—Fibrous.

*Soil.*—Plant in well drained, moisture retentive soil that is moderately fertile.

*Sunlight.*—Plant in full sunlight.

*Time to initiate roots.*—2 weeks are required for an initial cutting to produce roots.

*Crop time.*—10 to 12 months are required to produce a finished one-gallon plant in bud and flower from a rooted cutting.

*Seasonal interest.*—Spring foliage color and spring-summer flowering.

Stem:

*Branching habit.*—Naturally basal branching, with lateral branches emerging at approximately 40° to 45° from subtending stems. Branching is increased by pruning.

*Internode length.*—1.5 cm to 3.0 cm.

*Stem dimensions.*—Up to 35 cm in length, 2.5 mm in diameter.

*Stem shape.*—Cylindrical.

*Stem surface.*—Puberulent

*Stem color.*—Juvenile 153D, becoming 178A as matures and stiffens.

*Stem strength.*—Strong and wiry, becoming stiff with maturity.

Foliage:

*Type.*—Deciduous.

*Leaf arrangement.*—Alternate.

*Quantity of leaves.*—Approximately 50 per stem including lateral branches.

*Leaf division.*—Simple.

*Leaf aspect.*—Concave (upper surface) around central vein, becoming flat with maturity.

*Leaf shape.*—Ovate.

*Leaf base.*—Cuneate.

*Leaf apex.*—Acute.

*Leaf venation.*—Pinnate. Veins prominent and raised on abaxial surface.

*Vein color.*—As surrounding leaf surface (both surfaces) ranging from 53A in early spring to 146A by mid-summer.

*Leaf surface* (*both surfaces*).—Glabrous, dull.

*Leaf margin.*—Crenulate.

*Leaf attachment.*—Petiolate.

*Petiole dimensions.*—3 mm in length and 1 mm in diameter.

*Petiole color* (*summer*).—145A.

*Leaf length.*—2.5 cm to 6.0 cm.

*Leaf width.*—1.5 cm to 3.0 cm.

*Leaf color.*—Newly emerging shoot tip growth (both surfaces) ranges between 53A and 187C, becoming 137A (adaxial surface) and 146A with age.

Inflorescence:

*Type.*—Terminal dome-shaped compound corymb comprised of many umbellets consisting of three buds and flowers and borne on short pedicels.

*Diameter of corymb.*—3 cm in diameter.

*Quantity of buds and flowers.*—Approximately 30 per corymb.

*Buds.*—Bud shape: Globose. Bud color: Ranges between 60A and 67A. Bud surface: Puberulent. Bud dimensions: 3 mm in length and 3 mm in diameter.

*Flowers.*—Blooming period: Spring and summer. Persistent or self-cleaning: Self-cleaning. Each flower lasts for approximately 5 days. Entire inflorescence shows color for up to 14 days. Fragrance: Absent. Shape of flower: Rotate. Aspect: Facing upwards. Petals: Five in number. Color of petals: N66A aging to 55D. Petal base and corolla tube (inner surface) 53B. Shape of petal: Ovate. Fused or unfused: Petals are unfused. Dimensions of petal: 3 mm in length and 3 mm in width. Calyx shape: Campanulate, five ovate sepals fused at base. Calyx dimensions: 4 mm in diameter, sepals 3 mm in length, 2 mm in width. Calyx color, surface: 145A, Puberulent.

*Peduncle*.—Shape: Cylindrical, 1.0 cm to 1.5 cm in length, 1 mm in diameter. Color: 187A. Surface: Glabrous, glossy.

*Pedicel*.—Shape: Cylindrical, 4 mm to 5 mm in length, 0.5 mm to 1 mm in diameter. Color: 187C. Surface: Glabrous, glossy.

Reproductive organs:

*Stamens*.—Approximately 30 in number, clustered within calyx tube and exserted (anthers protruding) by 3 mm to 4 mm above petal arrangement.

*Filaments*.—4 mm to 6 mm in length, less than 0.5 mm in width, color 67D.

*Anthers*.—Globose, 1 mm in diameter, color NN155C to 156C.

*Pollen*.—Not observed.

*Pistil*.—Five in number, style 1 mm to 2 mm in length, color 59D.

*Stigma*.—Globose, color 53B.

*Ovary*.—Not observed.

Fruit and seed: None observed to date.

Diseases and pests: None known to the inventor.

COMPARISON WITH PARENTAL VARIETY

The inventor has not retained the immediate parent of 'Walplum'. 'Walplum' is a third generation seedling from *Spiraea japonica* 'Goldflame'. Whereas 'Walplum' has been repeatedly observed to be stable, plants of 'Goldflame' will produce leaves and shoots which are partly or fully reverted from gold to dark green. In addition, 'Goldflame' achieves a mature height around 90 cm whereas the mature height of 'Walplum' is 60 cm.

COMPARISON WITH KNOWN VARIETY

The variety of *Spiraea japonica* which most closely resembles 'Walplum' is the inventor's variety 'Walbuma' (U.S. Plant Pat. No. 9,363) which arose from the same breeding program. Whereas the emerging shoot tips of 'Walbuma' are red in color, the tips of 'Walplum' are deep red-purple in color. The mature foliage of 'Walbuma' is gold-green in color whereas the mature foliage of 'Walplum' is dark olive-green in color. In addition, whilst 'Walplum' exhibits a compact habit, plants of 'Walbuma' are more compact with smaller leaves and shorter internodes.

I claim:

1. A new and distinct cultivar of *Spiraea* plant named 'Walplum' as described and illustrated herein.

* * * * *